(12) United States Patent
Schaeffer (10) Patent No.: US 7,578,840 B2
(45) Date of Patent: Aug. 25, 2009

(54) STENT WITH REDUCED PROFILE

(75) Inventor: Darin Schaeffer, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 828 days.

(21) Appl. No.: 10/813,903

(22) Filed: Mar. 31, 2004

(65) Prior Publication Data

US 2005/0222670 A1  Oct. 6, 2005

(51) Int. Cl.
*A61F 2/06* (2006.01)
(52) U.S. Cl. ........................................ 623/1.15
(58) Field of Classification Search ............... 623/1.15, 623/1.16, 1.18, 1.2, 1.1, 1.11; 606/191–198
See application file for complete search history.

(56) References Cited

U.S. PATENT DOCUMENTS

| | | |
|---|---|---|
| 5,133,732 A | 7/1992 | Wiktor |
| 5,139,480 A | 8/1992 | Hickle |
| 5,195,984 A | 3/1993 | Schatz |
| 5,242,399 A | 9/1993 | Lau |
| 5,314,444 A | 5/1994 | Gianturco |
| 5,421,955 A | 6/1995 | Lau |
| 5,425,739 A | 6/1995 | Jessen |
| 5,441,515 A | 8/1995 | Khosravi |
| 5,443,477 A | 8/1995 | Marin |
| 5,494,029 A | 2/1996 | Lane |
| 5,496,277 A | 3/1996 | Termin |
| 5,507,767 A | 4/1996 | Maeda |
| 5,507,771 A | 4/1996 | Gianturco |
| 5,514,154 A | 5/1996 | Lau |
| 5,522,882 A | 6/1996 | Gaterud |
| 5,531,741 A | 7/1996 | Baracci |
| 5,549,662 A | 8/1996 | Fordenbacher |
| 5,843,175 A | 12/1998 | Frantzen |
| 5,868,782 A | 2/1999 | Frantzen |
| 6,042,606 A * | 3/2000 | Frantzen ............ 623/1.18 |
| 6,231,598 B1 | 5/2001 | Berry et al. |
| 6,302,917 B1 | 10/2001 | Dua et al. |
| 6,464,720 B2 | 10/2002 | Boatman et al. |
| 6,540,775 B1 | 4/2003 | Fischell et al. |
| 6,579,310 B1 * | 6/2003 | Cox et al. ............ 623/1.15 |
| 2002/0123791 A1 | 9/2002 | Harrison |
| 2002/0198593 A1 | 12/2002 | Gomez et al. |
| 2003/0069630 A1 | 4/2003 | Burgermeister et al. |

* cited by examiner

*Primary Examiner*—Kevin T Truong
(74) *Attorney, Agent, or Firm*—Brinks Hofer Gilson & Lione (57) ABSTRACT

A stent is provided which can be crimped to a reduced profile with reduced stress in the stent, while maintaining the strength and flexibility of the stent so that it can be advanced through the narrow passageways present in a patient's body and then expanded to dilate and/or circumferentially support the vessel wall. Also provided is a method of deploying such a stent.

41 Claims, 5 Drawing Sheets

STENT WITH REDUCED PROFILE

BACKGROUND

This invention relates to a radially expandable stent having a reduced profile in the unexpanded state.

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Still other stents are self-expanding. Regardless of the expansion method, expandable stents exhibit sufficient rigidity after being expanded that they will remain expanded after the catheter has been removed.

Radially expandable stents come in a variety of different configurations to provide optimal performance in various different particular circumstances. For instance, the patents to Lau (U.S. Pat. Nos. 5,514,154, 5,421,955, and 5,242,399), Baracci (U.S. Pat. No. 5,531,741), Gaterud (U.S. Pat. No. 5,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662) and Wiktor (U.S. Pat. No. 5,133,732), each include some form of radially expandable stent for implantation into a body lumen.

Figure 1:
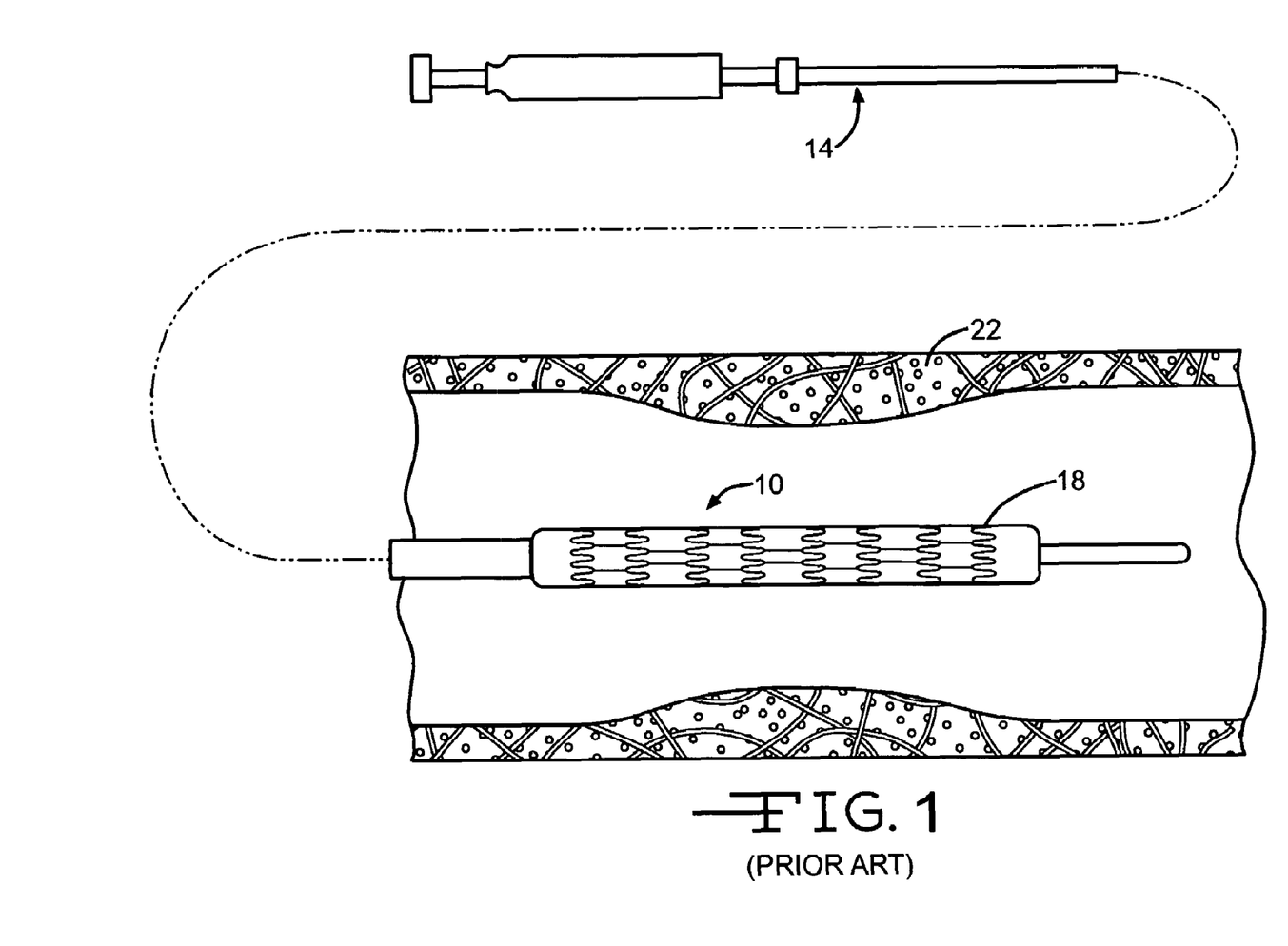
FIG. 1 is a partial view of a prior art stent mounted on a catheter device in a pre-deployment configuration.
Figure 2:
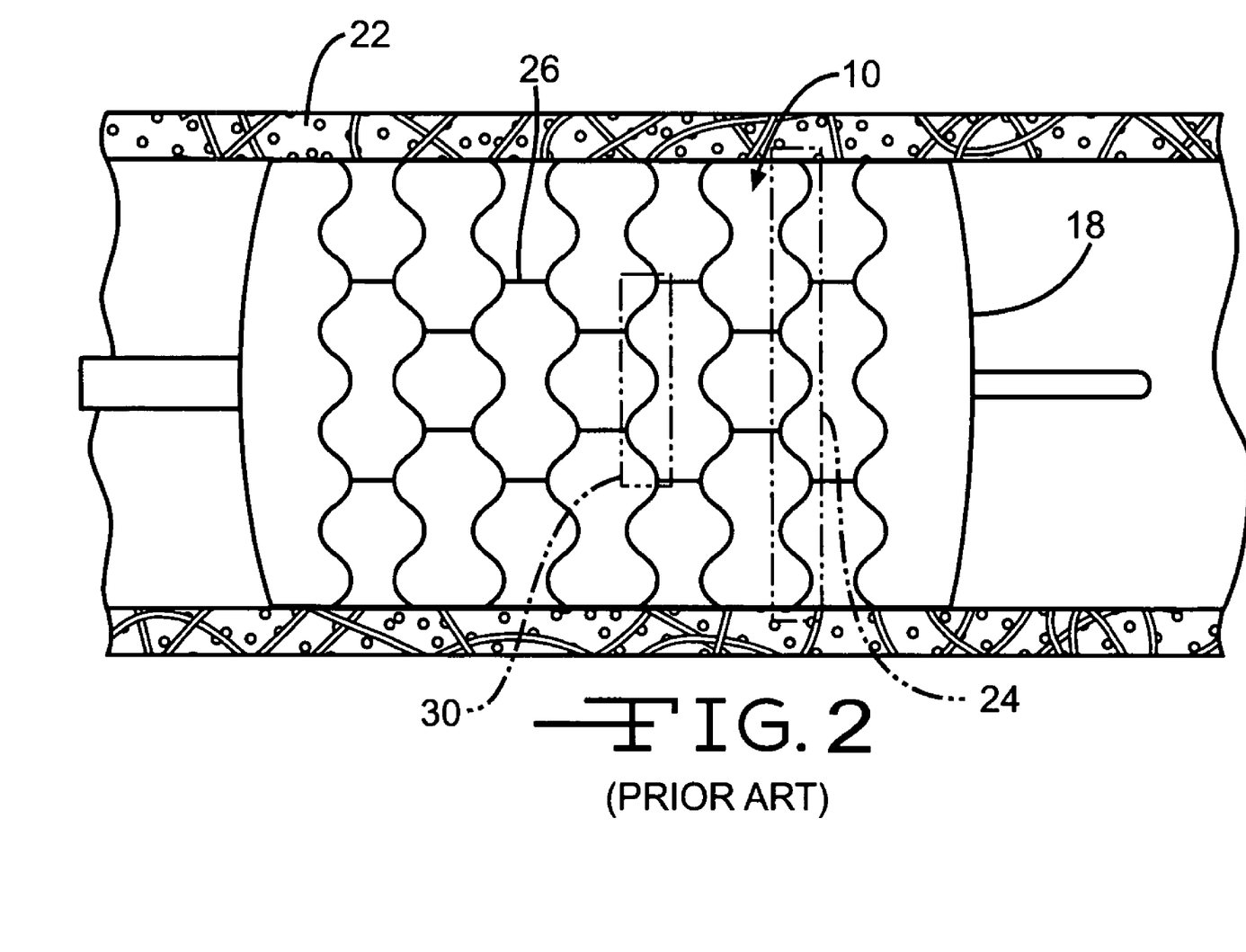
FIG. 2 is a partial view of the prior art stent of FIG. 1 expanded within an artery.
Figure 3:
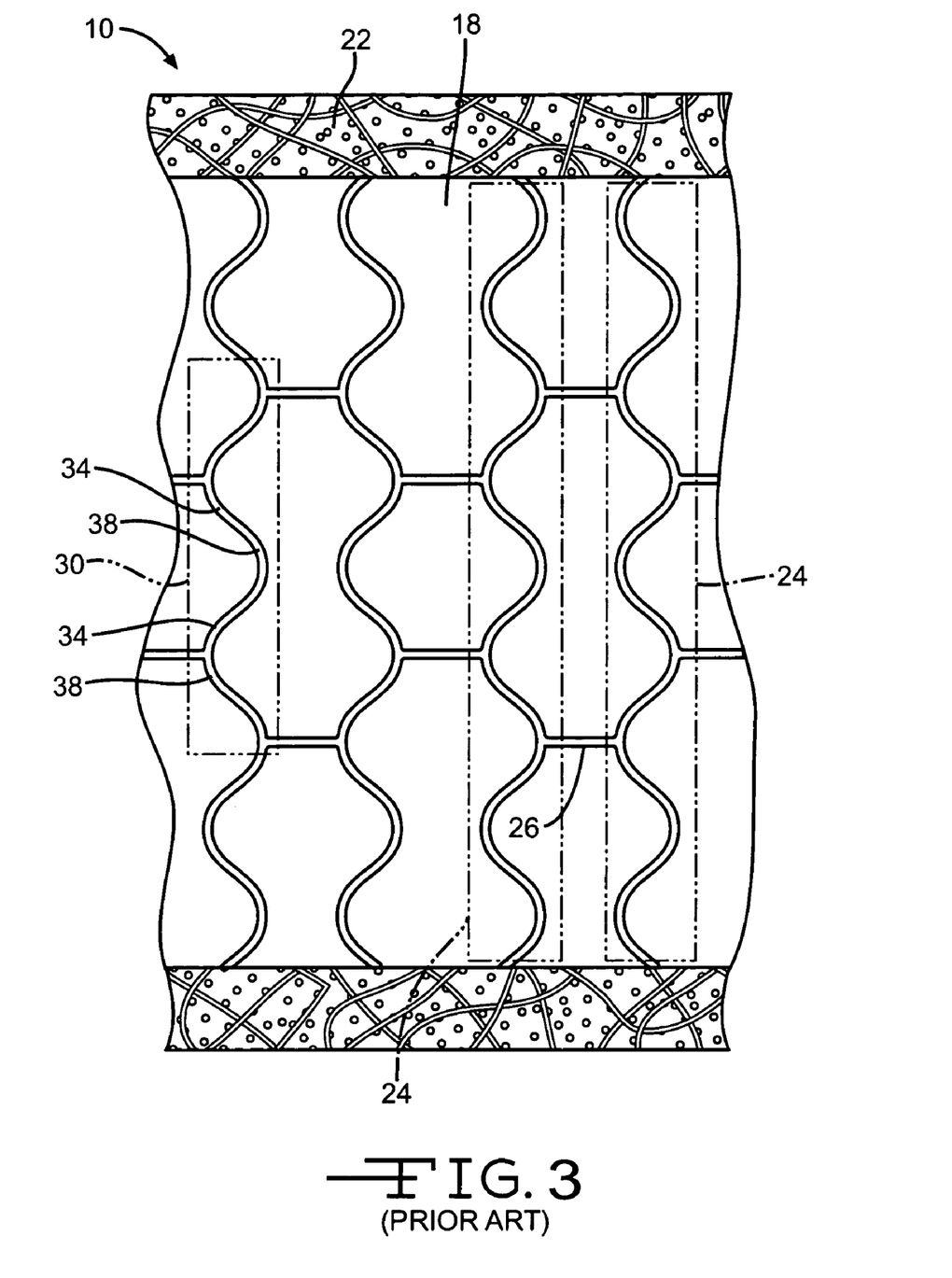
FIG. 3 is an enlarged partial view of the prior art stent of FIG. 2 in an expanded configuration within an artery.

As the above listed patents demonstrate, a wide variety of stents are known in the prior art. Typically, stents are tube-shaped. FIGS. 1-3 show an example of a prior art stent. As shown, the prior art stents often comprise a plurality of cylindrical, serpentine rings joined by connecting members. For deployment, stents are usually compressed to a low profile and crimped onto a catheter, and advanced through tortuous passageways in a patient's body to be deployed into a blood vessel or other body lumen where they are radially expanded.

FIG. 1 shows a prior art stent 10 mounted on a catheter device 14 in a pre-deployment configuration. Before insertion into a patient's body, the stent 10 is placed over the expandable balloon 18 and crimped onto the balloon in order to form a reduced profile for insertion into the body through small diameter, tortuous-pathed arteries or other vessels or lumens within the body. In other prior art systems, a self-expanding stent may be utilized. Typically, the catheter device 14 is advanced through a patient's body by deploying a small guide wire (not shown) and advancing the catheter device over the guide wire to its final destination such as a partially blocked artery 22. The balloon 18 is then inflated by methods known in the art to expand the stent radially so that the stent abuts against the walls of the artery as shown in FIG. 2. After deployment, the balloon is deflated, and the catheter device is removed from the patient's body. The stent 10 remains in the expanded configuration in the artery to hold the artery open and prevent further blockage.

However, prior art stents typically have problems with their ability to be crimped to a low profile for deployment into an artery or blood vessel. This makes it difficult to deliver the stent to its deployment location inside a small diameter, tortuous pathed artery. Additionally, the configurations of the prior art stents typically lead to problems with high stresses at various portions of the stent when crimped.

For example, FIG. 3 shows an enlarged view of the prior art stent 10 of FIG. 2 in an expanded configuration within an artery 22. The stent 10 utilizes a plurality of ring structures 24 interconnected by a plurality of generally straight connector members 26. In other prior art, the connector members 26 may have curved portions, such as U, V, or W shaped portions. Each ring structure 24 comprises an endless pattern of unit structures 30. The unit structures 30 are made up of a repeated pattern of a plurality of struts 34 joined together by bends or apexes 38. However, the configuration of the connector members 26 and bends 38 leads to increased stress in the stent 10 at the bends when the stent is in a crimped configuration prior to expansion within an artery. In an effort to alleviate this problem, some prior art stents have used stress-relieving bends (or apexes), which have bends extending outwardly from the struts in a key-hole shape or other outwardly extending shape, to reduce bending stresses. However, in many prior art stents utilizing stress-relieving bends, in the crimped, non-expanded configuration the bends 38 abut against each other thereby limiting how far the stent 10 may be crimped. As a result, it is more difficult to deliver these stents to their deployment location inside a vessel due to their enlarged profile.

What is needed is a stent which can be crimped to a reduced profile with reduced stress on the stent, while maintaining the strength and flexibility of the stent so that it can be advanced through the narrow passageways present in a patient's body and then expanded to dilate and/or circumferentially support the vessel wall. The present invention satisfies these and other needs.

SUMMARY

It is in an object of the invention to provide an expandable stent which can be crimped to a reduced profile with reduced stress in the stent, while maintaining the strength and flexibility of the stent so that it can be advanced through the narrow passageways present in a patient's body and then expanded to dilate and/or circumferentially support the vessel wall.

In one aspect, an expandable stent comprises a plurality of serpentine ring structures. Each of the ring structures comprises at least one unit structure. The unit structure comprises a plurality of bends at least some of which are key-hole shaped and positioned in a staggered arrangement to avoid abutment of the key-hole shaped bends against one another when the stent is in an unexpanded state. In addition, the unit structure comprises a plurality of strut members, wherein each of the key-hole shaped bends has a first end connected to one of the strut members and a second end connected to another of the strut members. In differing embodiments, the unit structure may comprise varying configurations. At least one connector member joins two of the ring structures. The connector member has a first end joined to a peak of one of the bends of one of the two ring structures and a second end joined to a peak of one of the bends of the other of the two ring structures.

In another aspect, an expandable stent comprises a plurality of cylindrical, serpentine ring structures. Each of the ring structures comprises an endless pattern of unit structures. Each of the unit structures comprises a plurality of strut members and a plurality of bends, at least some of which are key-hole shaped and positioned in a staggered arrangement to avoid abutment of the key-hole shaped bends against one another when the stent is in an unexpanded state. Each of the plurality of bends communicates with two of the plurality of strut members. At least two of the unit structures are adjacent and joined together by first and second tie-bars. The plurality of strut members and plurality of bends of the at least two adjacent unit structures are disposed substantially between the first and second substantially straight tie-bars. Further included is at least one connector member having a curved portion joining two of the ring structures. The connector member has a first end joined to a peak of one of the bends of one of the two ring structures and a second end joined to a peak of one of the bends of the other of the two ring structures.

In yet another aspect, a method of deploying a stent comprises providing an expandable stent. The stent comprises a plurality of serpentine ring structures. Each of the ring structures comprises at least one unit structure. The unit structure comprises a plurality of bends at least some of which are key-hole shaped, a plurality of strut members, and at least one connector member joining two of the ring structures. Each of the bends has a first end connected to one of the strut members and a second end connected to another of the strut members. In other embodiments, the unit structure may comprise different configurations. The connector member has a first end joined to a peak of one of the bends of one of the two ring structures and a second end joined to a peak of one of the bends of the other of the two ring structures. The stent is crimped to a pre-deployment configuration in which the stent is in an unexpanded state and the key-hole shaped bends are positioned in a staggered arrangement to avoid abutment of the key-hole shaped bends against one another. Next, the stent is delivered into a patient's body to a desired deployment site. The stent is then expanded.

The expandable stent of the invention allows the stent to be crimped (collapsed, restrained) to a reduced profile with reduced stress in the stent, while maintaining the strength and flexibility of the stent so that it can be advanced through narrow passageways in a patient's body and expanded to support a vessel wall.

The present invention, together with further objects and advantages, will be best understood by reference to the following detailed description taken in conjunction with the accompanying drawings.

DETAILED DESCRIPTION OF THE PREFERRED EMBODIMENTS

The following description of preferred embodiments of the invention provides examples of the present invention. The embodiments discussed herein are merely exemplary in nature, and are not intended to limit the scope of the invention in any manner. Rather, the description of these preferred embodiments serves to enable a person of ordinary skill in the art to make and use the present invention.

As shown in the drawings for purposes of illustration, the present invention is directed to a low profile, reduced stress, radially expandable stent. The invention is applicable to stents having different types of configurations and different deployment systems, such as self-expanding or balloon expandable systems as known in the art.

The present invention solves some of the problems of the prior art by providing a stent which can be crimped (collapsed, restrained) in an unexpanded state to a lower profile in a configuration placing reduced stress in the stent, while maintaining the strength and flexibility of the stent so that it can be advanced through the narrow passageways present in a patient's body and then expanded to dilate and/or circumferentially support the vessel wall. Preferably, the stent of the present invention is delivered into the patient's body by advancing a catheter device over a guide wire.

Figure 4:
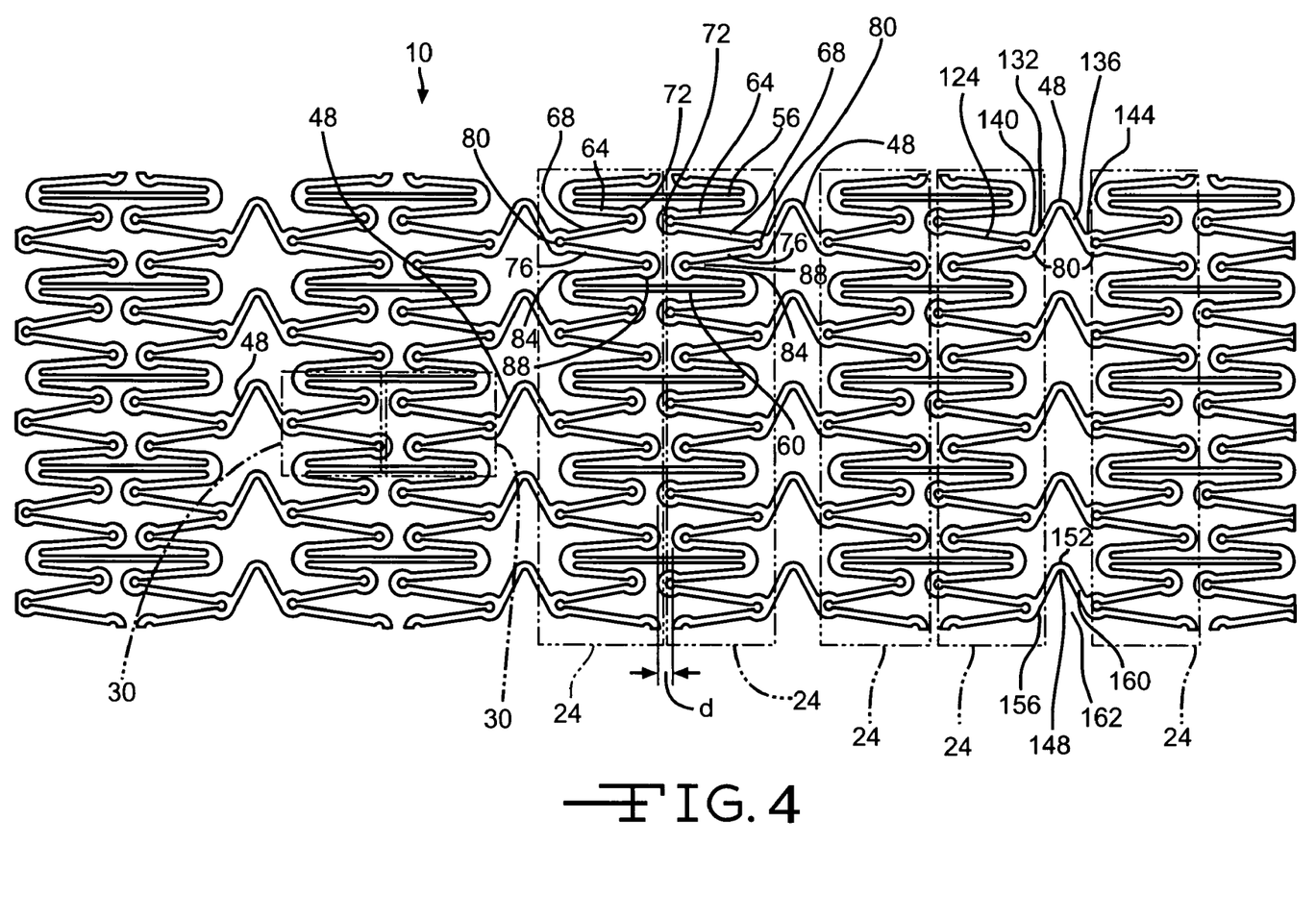
FIG. 4 is a partial plan view of a preferred embodiment of the stent of the present invention in a partially expanded configuration.

FIG. 4 illustrates a stent 10 in a slightly expanded configuration according to a preferred embodiment of the invention. The stent 10 comprises a plurality of serpentine (zig-zag or undulating) ring structures 24 interconnected by a plurality of connector members 48. Each ring structure 24 is a substantially circular ring comprising an endless pattern of unit structures 30. The unit structure 30 represents a specific configuration of the wire members, including the struts and bends.

Preferably, as illustrated in FIG. 4, some adjacent unit structures 30 of adjacent ring structures 24 are connected together by first and second tie-bars 56 and 60. The repeated unit structure 30 of each ring structure 24 preferably comprises first and second struts 64 and 68 joined together by a first key-hole shaped bend 72, a third strut 76 joined to the second strut 68 by a second key-hole shaped bend 80, and a fourth strut 84 joined with the third strut 76 by a third key-hole shaped bend 88. In other embodiments the unit structure 30 may include a different number of struts and bends in varying configurations. The term "key-hole shaped bend" simply denotes that the bend is expanded or bulbous. In some embodiments, a "key-hole shaped bend" may be expanded in a key-hole shape, but in other embodiments it may be expanded in configurations other than a key-hole shape. This expansion reduces stresses in the region of the bend and provides the connected struts with greater expansion potential. The first strut 64 is the shortest strut, while the third strut 76 is the longest strut. The second strut 68 and fourth strut 84 are similar in length. In other embodiments, varying lengths may be used for the struts. The first key-hole shaped bend 72 is disposed axially apart from the third key-hole shaped bend 88 by a distance d. This distance d between the first and third key-hole shaped bends 72 and 88 prevents the bends from abutting against each other and allows the stent to be crimped down more than it would if the bends were aligned. As a result, the stent profile can be made smaller and the stent more easily inserted into a small, tortuous-pathed vessel.

The struts and bends of the unit structure 30 preferably form repeated U or V shapes 124, but in other embodiments may be in other configurations. The U or V shapes 124 provide many advantages, such as being easily repeated around the circumference of the ring structures 24. Additionally, the U or V shapes 124 facilitate the staggered arrangement of bends. Another advantage of using the U or V shapes 124 is the availability of central attachment points for connecting members, as is more fully described below.

The ring structures 24 are interconnected to form the stent 10 by a plurality of connector members 48. As illustrated in FIG. 4, each connector member 48 joins first and second ring structures 24 and is preferably disposed between two adjacent unit structures 30. Each connector member 48 has a first end 132 and a second end 136. The first end 132 of each connector member 48 is joined to a peak 140 of the second bend 80 of each unit structure 30 on one ring structure 24. The second end 136 of each connector member 48 is joined to a peak 144 of the second bend 80 of an adjacent unit structure 30 on an adjacent ring structure 24. In other embodiments, varying configurations may be used to join the adjacent unit structures 30 of the ring structures 24 with the connector members 48. For example, the connector members 48 may join adjacent first bends 72 of adjacent unit structures 30 on separate ring structures 24, or may join adjacent third bends 88 of adjacent unit structures 30 on separate ring structures 24. As illustrated in FIG. 4, it is preferable that each unit structure 30 of each ring structure 24 is connected to two connector members 48. In other embodiments, a varying number of connector members 48 may be used to join each ring structure 24.

In addition to the first and second ends 132 and 136, each connector member 48 also includes an undulating portion 148. The undulating portion 148 provides longitudinal flexibility and makes the stent 10 more flexible to bend during delivery. A variety of configurations can be used for the undulating portion 148, such as U, V, W, or Z shapes. The connector segments shown in FIG. 4 illustrate a preferred configuration for the undulating portions 148. In this preferred embodiment, each undulating portion 148 comprises an inverted "V" shape 152 made up of first and second legs 156 and 160. This configuration simplifies manufacture while providing the desired undulating portion 148 that confers axial flexibility onto the stent 10.

As illustrated in FIG. 4, it is preferable that the undulating portion 148 be positioned in the space 162 between each ring structure 24 without being overlapped by any of the tie-bars 56 and 60, struts 64, 68, 76, and 84, or bends 72, 80, and 88 of the adjacent unit structures 30. This allows the maximum possible flexibility of the undulating portion 148 by avoiding any potential abutment against the undulating portion 148. This configuration provides the desired axial flexibility while maintaining radial strength of the stent 10. Also, this configuration facilitates manufacturing due to the use of aligned portions. In other embodiments the undulating portion 148 may overlap the above-referenced members.

As illustrated in FIG. 4, adjacent ring structures 24 are preferably radially aligned with each other. That is, adjacent ring structures 24 are preferably aligned such that axially adjacent unit structures 30 lie in complementary position relative to each other. Particularly preferable, all ring structures 24 of the stent 10 are radially aligned in this manner. However, other configurations may be used including staggered adjacent ring structures 24. As shown, it is preferable that the connector members 48 joining adjacent ring structures 24 are in circumferential alignment relative to one another. This preferred arrangement arises due to the uniformity of the "V" shaped connecting members 48 and unit structures 30, all arranged in alignment with one another. This arrangement maintains the desired axial flexibility while also contributing to the radial strength of the stent 10 and facilitating manufacturing. In other embodiments, the connector members 48 joining adjacent ring structures 24 may be circumferentially displaced relative to one another.

Figure 5:
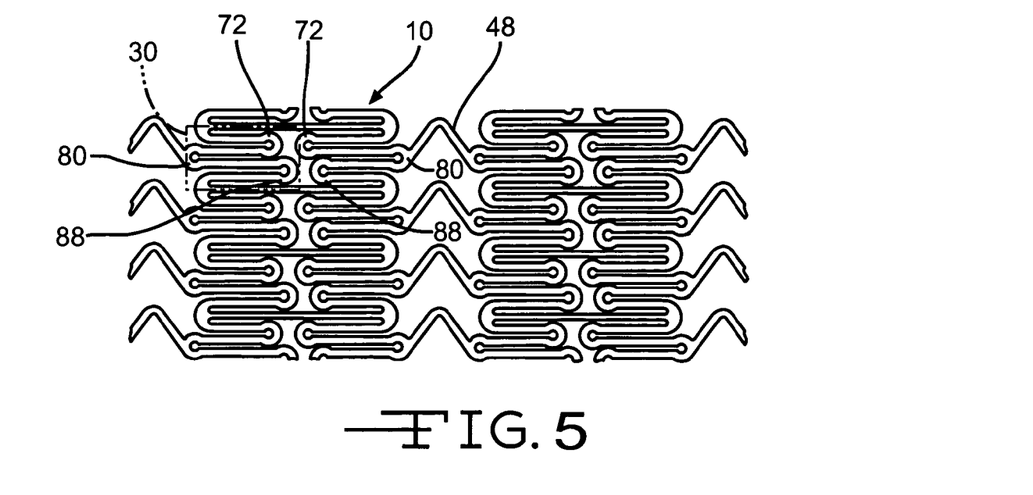
FIG. 5 is a partial plan view of the unit structure of the stent of FIG. 4 in an unexpanded configuration.

The stent 10 is an expandable stent having radially unexpanded and expanded configurations. Also, the stent 10 can be either a self-expanding stent, such as one fabricated from a shape memory material such as Nitinol, or a balloon expandable stent. FIG. 5 illustrates the stent 10 of FIG. 4 in its radially unexpanded configuration. In this configuration, which is conventionally used to minimize the radial dimension of the stent in order to facilitate placement into and navigation through a narrow body vessel, the connector members 48 are preferably arranged in the circumferentially aligned manner as shown and described above. As shown, the staggered arrangement of the first, second, and third key-hole shaped bends 72, 80, and 88, effectively prevents each of the respective bends from abutting against one another when the stent is in its radially unexpanded configuration. As a result, the stent 10 is crimped to a lower profile, and the lower profile aids in the delivery of the stent through small diameter, tortuous pathed vessels.

Figure 6:
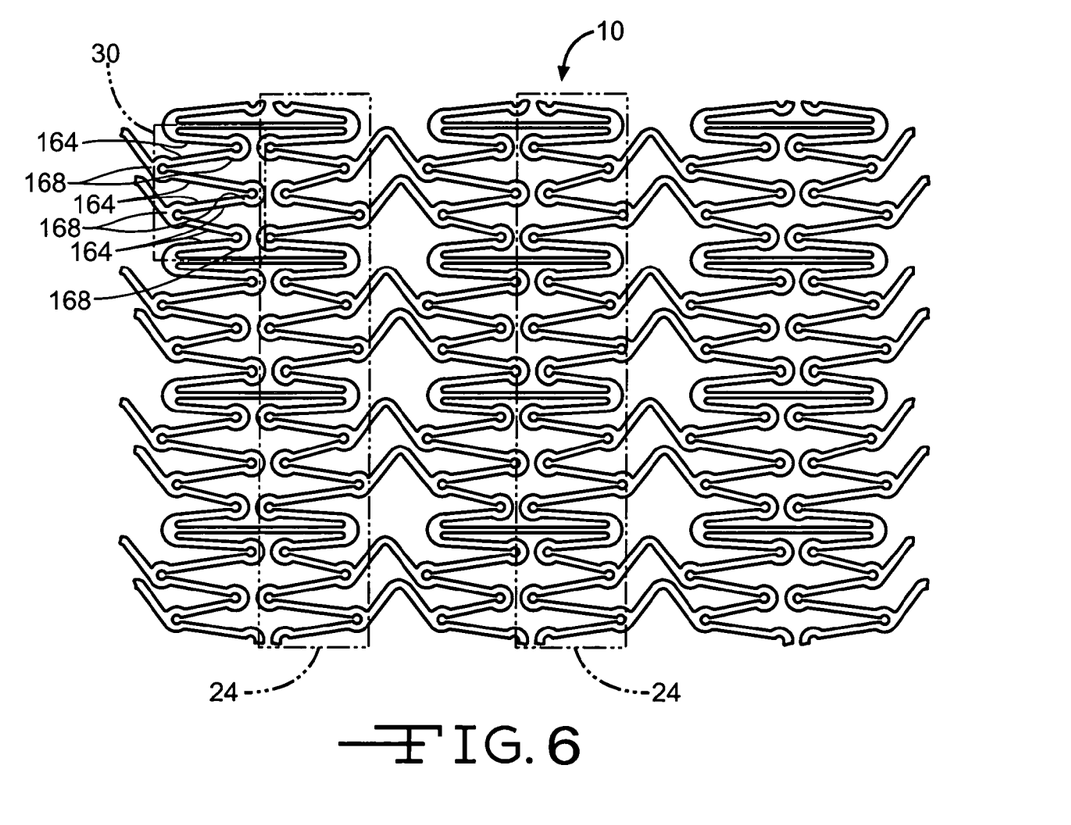
FIG. 6 is a partial plan view of the unit structure of another embodiment of the stent of the present invention in a partially expanded configuration.

FIG. 6 illustrates a stent 10 according to another embodiment of the present invention. In this embodiment the stent 10 includes a modified unit structure 30. The remainder of the stent, including the ring structure 24 is preferably the same as described above for the preferred embodiment. In this embodiment, the unit structure 30 is modified to include six struts 164 and five key-hole shaped bends 168 in a staggered arrangement. In other embodiments, the unit structure may be modified to include a varying number of struts, and key-hole shaped bends in staggered arrangement.

Stents according to the present invention can be fabricated by any suitable process known in the art. The fabrication process need only be able to produce the ring architecture and connector segments of the invention. For self-expanding stents, a thread of suitable material can be weaved and/or configured into appropriate form, or the stent may be laser cut out of a tube of appropriate material. For balloon-expanded stents, the stent is preferably fabricated from an initially solid tube of appropriate material by etching or cutting away unused portions to leave a stent with the desired pattern.

The stent can also be fabricated from any suitable material. The material need only be medically acceptable, i.e., biocompatible, and provide the desired longitudinal flexibility and radial strength. Examples of suitable materials include shape memory alloys, such as Nitinol, stainless steel, cobalt-chrome alloys, and amorphous metal alloys.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that the appended claims, including all equivalents thereof, are intended to define the scope of the invention.

The invention claimed is:

1. An expandable stent comprising: a plurality of serpentine ring structures, wherein at least one of said ring structures comprises a first key-hole shaped bend disposed at a first longitudinal end of said ring structure and a second key-hole shaped bend disposed at said same first longitudinal end of said ring structure, said first and second key-hole shaped bends being disposed circumferentially adjacent to one another at said same end of said same ring structure and being longitudinally staggered with respect to one another, said first and second key-hole shaped bends thereby avoiding abutment against one another when said stent is in an unexpanded state, and a plurality of strut members, wherein each of said first and second key-hole shaped bends has a first end connected to one of said strut members and a second end connected to another of said strut members, said strut members extending away from said first and second key-hole shaped bends in substantially the same direction; and at least one connector member joining two of said ring structures, said at least one connector member having a first end joined to a peak of one of said bends of one of said two ring structures and a second end joined to a peak of one of said bends of the other of said two ring structures.

2. The expandable stent of claim 1, wherein said bends which said connector member is joined to are key-hole shaped.

3. The expandable stent of claim 1, wherein each unit structure of each of said plurality of ring structures is in communication with at least one connector member.

4. The expandable stent of claim 1, wherein there are two or more connector members joining said two ring structures and said connector members are circumferentially aligned.

5. The expandable stent of claim 1, wherein adjacent ring structures are axially aligned.

6. The expandable stent of claim 1, wherein some adjacent unit structures are joined together by first and second substantially straight tie-bars.

7. The expandable stent of claim 6, wherein said plurality of bends are positioned substantially between said first and second substantially straight tie-bars.

8. The expandable stent of claim 1, wherein said at least one connector member is one of U, V, and W shaped.

9. The expandable stent of claim 1, wherein said unit structure comprise three key-hole shaped bends.

10. The expandable stent of claim 1, wherein two of said strut members form a substantially V-shape.

11. The expandable stent of claim 1, wherein said at least one connector member joins adjacent substantially aligned bends of adjacent ring structures.

12. The expandable stent of claim 1, wherein said ring structures are cylindrical.

13. The expandable stent of claim 1, wherein each of said ring structures comprise an endless pattern of unit structures.

14. The expandable stent of claim 1, wherein the expandable stent is self-expanding.

15. The expandable stent of claim 1, wherein the expandable stent is adapted to be expanded using a balloon.

16. An expandable stent comprising: a plurality of cylindrical, serpentine ring structures, wherein at least one of said ring structures comprises a plurality of strut members, a first key-hole shaped bend disposed at a first longitudinal end of said ring structure, and a second key-hole shaped bend disposed at said same first longitudinal end of said ring structure, wherein each of said first and second key-hole shaped bends has a first end connected to one of said strut members and a second end connected another of said strut members, said strut members extend away from said first and second key-hole shaped bends in substantially the same direction, said first and second key-hole shaped bends being disposed circumferentially adjacent to one another at said same end of said same ring structure and being longitudinally staggered with respect to one another, said first and second key-hole shaped bends thereby avoiding abutment against one another when the stent is in an unexpanded state, wherein at least two of said unit structures are adjacent and joined together by first and second tie-bars with said plurality of strut members and said plurality of bends of said at least two adjacent unit structures being disposed substantially between said first and second substantially straight tie-bars; and at least one connector member having a curved portion joining two of said ring structures, wherein said at least one connector member has a first end joined to a peak of one of said bends of one of said two ring structures and a second end joined to a peak of one of said bends of the other of said two ring structures.

17. The expandable stent of claim 16, wherein each unit structure of each of said plurality of ring structures is in communication with at least one connector member.

18. The expandable stent of claim 16, wherein there are two or more connector members joining said two ring structures and said connector members are circumferentially aligned.

19. The expandable stent of claim 16, wherein adjacent ring structures are axially aligned.

20. The expandable stent of claim 16, wherein said unit structure comprise three key-hole shaped bends.

21. The expandable stent of claim 16, wherein two of said strut members form a substantially V-shape.

22. The expandable stent of claim 16, wherein said at least one connector member joins adjacent substantially aligned bends of adjacent ring structures.

23. The expandable stent of claim 16, wherein the expandable stent is self-expanding.

24. The expandable stent of claim 16, wherein the expandable stent is adapted to be expanded using a balloon.

25. The expandable stent of claim 16, wherein said at least one connector member is one of U, V, and W shaped.

26. The expandable stent of claim 16, wherein each of said bends has a first end connected to one of said strut members and a second end connected to another of said strut members.

27. The expandable stent of claim 16, wherein said bends which said connector member is joined to are key-hole shaped.

28. The expandable stent of claim 1, further comprising first and second tie-bars connecting at least one of said two ring structures to another ring structure, said plurality of bends and said struts being positioned substantially between said first and second tie-bars, wherein said plurality of bends comprises first, second and third key-hole shaped bends and said struts comprise first, second, third and fourth struts, said first and second struts are joined together by said first key-hole shaped bend, said third strut is joined to said second strut by said second key-hole shaped bend, and said fourth strut is joined with said third strut by said third key-hole shaped bend, said first strut being joined to said first tie-bar and said fourth strut being joined to said second tie-bar.

29. The expandable stent of claim 28, wherein said unit structure consists of one of said connector members, said connector member being joined to said second key-hole shaped bend.

30. The expandable stent of claim 29, wherein said first key-hole shaped bend and said third key-hole shaped bend are positioned in said staggered arrangement relative to each other.

31. The expandable stent of claim 30, wherein said third strut is longer than said first strut.

32. The expandable stent of claim 31, wherein said connector member comprises a curved portion between said first end and said second end.

33. The expandable stent of claim 32, wherein said first and second tie-bars are substantially straight, said first key-hole shaped bend being positioned adjacent said first tie-bar and said third key-hole shaped bend being positioned adjacent said second tie-bar when the stent is in an unexpanded state.

34. The expandable stent of claim 1, further comprising first and second tie-bars connecting at least one of said two ring structures to another ring structure, said plurality of bends and said struts being positioned substantially between said first and second tie-bars, wherein said plurality of bends comprises first, second, third, fourth and fifth key-hole shaped bends and said struts comprise first, second, third, fourth, fifth and sixth struts, said first and second struts are joined together by said first key-hole shaped bend, said third strut is joined to said second strut by said second key-hole shaped bend, said fourth strut is joined with said third strut by said third key-hole shaped bend, said fifth strut is joined with said fourth strut by said fourth key-hole shaped bend, said sixth strut is joined with said fifth strut by said fifth key-hole shaped bend, said first strut being joined to said first tie-bar and said sixth strut being joined to said second tie-bar.

35. The expandable stent of claim 34, wherein said first key-hole shaped bend and said third key-hole shaped bend are positioned in said staggered arrangement relative to each other.

36. The expandable stent of claim 35, wherein said third key-hole shaped bend and said fifth key-hole shaped bend are positioned in said staggered arrangement relative to each other.

37. The expandable stent of claim 36, wherein said second key-hole shaped bend and said fourth key-hole shaped bend are positioned in said staggered arrangement relative to each other.

38. The expandable stent of claim 37, wherein said connector member is joined to said second key-hole shaped bend or said fourth key-hole shaped bend.

39. The expandable stent of claim 38, wherein said unit structure comprises two of said connector members, one of said two connector members being joined to said second key-hole shaped bend and another of said two connector members being connected to said fourth key-hole shaped bend.

40. The expandable stent of claim 39, wherein said connector members comprise a curved portion between said first end and said second end.

41. The expandable stent of claim 40, wherein said first and second tie-bars are substantially straight, said first key-hole shaped bend being positioned adjacent said first tie-bar and said fifth key-hole shaped bend being positioned adjacent said second tie-bar when the stent is in an unexpanded state.

* * * * *

UNITED STATES PATENT AND TRADEMARK OFFICE
CERTIFICATE OF CORRECTION

PATENT NO. : 7,578,840 B2
APPLICATION NO. : 10/813903
DATED : August 25, 2009
INVENTOR(S) : Darin Schaeffer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1103 days.

Signed and Sealed this

Seventh Day of September, 2010

David J. Kappos
*Director of the United States Patent and Trademark Office*